(12) United States Patent
Silberstein

(10) Patent No.: US 9,474,283 B2
(45) Date of Patent: Oct. 25, 2016

(54) FORMULATIONS COMPRISING SAPONINS AND USES THEREOF

(75) Inventor: Tova Silberstein, Jerusalem (IL)

(73) Assignee: Y&B Mother's Choice Ltd., Jerusalem (IL)

( * ) Notice: Subject to any disclaimer, the term of this patent is extended or adjusted under 35 U.S.C. 154(b) by 0 days.

(21) Appl. No.: 13/992,310

(22) PCT Filed: Dec. 8, 2011

(86) PCT No.: PCT/IL2011/050053
§ 371 (c)(1),
(2), (4) Date: Jun. 7, 2013

(87) PCT Pub. No.: WO2012/077119
PCT Pub. Date: Jun. 14, 2012

(65) Prior Publication Data
US 2013/0295204 A1    Nov. 7, 2013

Related U.S. Application Data

(60) Provisional application No. 61/421,440, filed on Dec. 9, 2010.

(51) Int. Cl.

| | |
|---|---|
| A61K 36/82 | (2006.01) |
| A61K 36/185 | (2006.01) |
| A61K 36/36 | (2006.01) |
| A61K 36/31 | (2006.01) |
| A61K 36/77 | (2006.01) |
| A01N 65/08 | (2009.01) |
| A61K 8/63 | (2006.01) |
| A61K 8/97 | (2006.01) |
| A61K 36/355 | (2006.01) |
| A61K 36/76 | (2006.01) |
| A61Q 19/00 | (2006.01) |
| A01N 43/16 | (2006.01) |
| A01N 45/00 | (2006.01) |
| A61K 31/704 | (2006.01) |
| A61Q 5/02 | (2006.01) |

(52) U.S. Cl.
CPC ............... *A01N 65/08* (2013.01); *A01N 43/16* (2013.01); *A01N 45/00* (2013.01); *A61K 8/63* (2013.01); *A61K 8/97* (2013.01); *A61K 31/704* (2013.01); *A61K 36/31* (2013.01); *A61K 36/355* (2013.01); *A61K 36/76* (2013.01); *A61K 36/77* (2013.01); *A61K 36/82* (2013.01); *A61Q 19/00* (2013.01); *A61K 2800/10* (2013.01); *A61K 2800/524* (2013.01); *A61Q 5/02* (2013.01)

(58) Field of Classification Search
None
See application file for complete search history.

(56) References Cited

U.S. PATENT DOCUMENTS

| | | |
|---|---|---|
| 2,996,540 A | 8/1967 | Pearl |
| 4,247,569 A | 1/1981 | Hata et al. |
| 4,511,555 A | 4/1985 | Faust |
| 5,080,901 A | 1/1992 | Hangay et al. |
| 5,397,778 A | 3/1995 | Forse et al. |
| 5,455,232 A | 10/1995 | Piljac et al. |
| 5,466,675 A | 11/1995 | Piljac et al. |
| 5,503,766 A | 4/1996 | Kulperger |
| 5,514,661 A | 5/1996 | Piljac et al. |
| 5,639,794 A | 6/1997 | Emerson et al. |
| 5,817,314 A | 10/1998 | So et al. |
| 6,475,476 B1 | 11/2002 | Fluker |
| 6,485,711 B1 | 11/2002 | Olmstead |
| 6,548,463 B2 | 4/2003 | Miyahara et al. |
| 7,001,877 B1 | 2/2006 | Grier |
| 7,129,218 B2 | 10/2006 | Stipcevic et al. |
| 7,262,171 B1 | 8/2007 | Piljac et al. |
| 2006/0018867 A1 | 1/2006 | Kawasaki et al. |
| 2007/0202062 A1 | 8/2007 | Workman et al. |
| 2007/0231403 A1 | 10/2007 | Park et al. |
| 2010/0055138 A1 | 3/2010 | Margulies et al. |
| 2010/0183528 A1 | 7/2010 | Maloney et al. |
| 2011/0020302 A1 | 1/2011 | Banov et al. |
| 2011/0052514 A1 | 3/2011 | Jüsten et al. |
| 2012/0129950 A1 | 5/2012 | Macinga et al. |

FOREIGN PATENT DOCUMENTS

| | | |
|---|---|---|
| AU | 747088 | 5/2002 |
| CA | 2 460 825 A1 | 9/2005 |
| CA | 2 195 419 C | 1/2008 |
| CA | 2 129 542 C | 4/2008 |
| CA | 2 378 557 C | 12/2009 |
| CA | 2 321 926 C | 4/2010 |
| CA | 2 658 873 A1 | 9/2010 |
| CN | 1056525 A | 11/1991 |
| CN | 1240640 A | 1/2000 |
| CN | 1344537 A | 4/2002 |
| CN | 1349792 A | 5/2002 |
| CN | 1370515 A | 9/2002 |
| CN | 101214208 A | 7/2008 |
| CN | 101390816 A | 3/2009 |

(Continued)

OTHER PUBLICATIONS

Nakano et al. (JP200265327A DWPI Abstract and full computer-assisted English Translation enclosed, Sep. 2002).*

(Continued)

*Primary Examiner* — Chris R Tate
*Assistant Examiner* — Randall Winston
(74) *Attorney, Agent, or Firm* — Vorys, Sater, Seymour & Pease LLP

(57) ABSTRACT

Provided is a formulation including various natural extracts for a variety of human applications.

14 Claims, No Drawings

(56) References Cited

FOREIGN PATENT DOCUMENTS

| | | | |
|---|---|---|---|
| CN | 101732208 A | 6/2010 | |
| CN | 101978844 A | 2/2011 | |
| CN | 102028640 A | 4/2011 | |
| CN | 102247309 A | 11/2011 | |
| CN | 102379836 A | 3/2012 | |
| EP | 1 053 782 A1 | 11/2000 | |
| EP | 1 287 742 A1 | 3/2003 | |
| EP | 1 889 623 A2 | 2/2008 | |
| ES | 2 259 933 A1 | 10/2006 | |
| FR | 2 730 634 A1 | 8/1996 | |
| FR | 2 924 123 A1 | 5/2009 | |
| JP | 52-125510 A | 10/1977 | |
| JP | 60-38317 A | 2/1985 | |
| JP | 64-68307 A | 3/1989 | |
| JP | 6-57298 A | 3/1994 | |
| JP | 9-503196 A | 3/1997 | |
| JP | 9-249577 A | 9/1997 | |
| JP | 10-502925 A | 3/1998 | |
| JP | 10-298595 A | 11/1998 | |
| JP | 2000-191513 A | 7/2000 | |
| JP | 2001322943 A | 11/2001 | |
| JP | 2002000447 A | 1/2002 | |
| JP | 2002-265327 A | 9/2002 | |
| JP | 2002265327 A | * 9/2002 | |
| JP | 2002-363065 A | 12/2002 | |
| JP | 2003096489 A | 4/2003 | |
| JP | 2003-267834 A | 9/2003 | |
| JP | 2004-631 A | 1/2004 | |
| JP | 2004-331961 A | 11/2004 | |
| JP | 2005343883 A | 12/2005 | |
| JP | 3860206 B2 | 12/2006 | |
| JP | 2007-223905 A | 9/2007 | |
| JP | 2008-120745 A | 5/2008 | |
| JP | 2008120745 A | * 5/2008 | |
| JP | 2009007266 A | 1/2009 | |
| JP | 2012-077037 A | 4/2012 | |
| KR | 10-0821842 B1 | 4/2008 | |
| KR | 10-0821846 B1 | 4/2008 | |
| KR | 2010-0077554 A | 7/2010 | |
| RO | 110679 B1 | * 3/1996 | |
| RU | 2 124 899 C1 | 1/1999 | |
| RU | 2 126 687 C1 | 2/1999 | |
| RU | 2 154 480 C1 | 8/2000 | |
| RU | 2 162 701 C1 | 2/2001 | |
| RU | 2 179 978 C1 | 2/2002 | |
| RU | 2 210 379 C1 | 8/2003 | |
| RU | 2 234 913 C1 | 8/2004 | |
| RU | 2 247 571 C2 | 3/2005 | |
| RU | 2328301 C2 | * 7/2008 | |
| TW | 200944244 A | 11/2009 | |
| WO | 93/14767 A2 | 8/1993 | |
| WO | 98/48768 A1 | 11/1998 | |
| WO | 99/43334 A1 | 9/1999 | |
| WO | 00/72861 A1 | 12/2000 | |
| WO | 01/10447 A1 | 2/2001 | |
| WO | 02/092823 A1 | 11/2002 | |
| WO | 03/097003 A1 | 11/2003 | |
| WO | 2005/099729 A2 | 10/2005 | |
| WO | 2006/007741 A1 | 1/2006 | |
| WO | 2008/013899 A2 | 1/2008 | |
| WO | 2009/153800 A1 | 12/2009 | |
| WO | 2012/077119 A2 | 6/2012 | |
| WO | 2012/077120 A2 | 6/2012 | |

OTHER PUBLICATIONS

U.S. Appl. No. 09/644,984; U.S. Pat. No. 7,262,171; 260 pages; (2000).
U.S. Appl. No. 11/701,860; 116 pages; (2007).
U.S. Appl. No. 11/881,271; U.S. Pat. No. 7,985,722; 186 pages; (2007).
U.S. Appl. No. 11/985,977; 85 pages; (2007).
Shiau, et al., "Quantification for Saponin from a Soapberry (Sapindus mukorossi Gaertn) in Cleaning Products by a Chromatographic and two Colorimetric Assays", J. Fac. Agr., Kyushu Univ., vol. 54, No. 1, pp. 215-221, (2009).
Natural Preservative—Aspen Bark Extract, online at http://www.theherbarie.com/Aspen-Bark-Extract-pr-463.html, four pages, retrieved online Jun. 10, 2013.
Natural Soap Recipe, online at http://www.essortment.com/natural-soap-recipe-38714.html, three pages, retrieved online Jun. 10, 2013.
Osbourn, et al., "The saponins—polar isoprenoids with important and diverse biological activities", Nat. Prod. Rep., vol. 28, pp. 1261-1268, (2011).
Saha, et al., "Structure-biological activity relationships in triterpenic saponins: the relative activity of protobassic acid and its derivatives against plant pathogenic fungi", Pest Manag Sci, vol. 66, pp. 825-831, (2010).
Huang, et al., "Triterpenoid saponins from the fruits and galls of Sapindus mukorossi", Phytochemistry, vol. 69, pp. 1609-1616, (2008).
Sea Kelp Moisturizer (high performance anti-aging moisturizer); online at http://www.benaturalorganics.com/details-sea-kelp-moisturizer.html, two pages, retrieved online Jun. 10, 2013.
Murgu, et al., "Dereplication of Glycosides from Sapindus saponaria using Liquid Chromatography-Mass Spectrometry", J. Braz. Chem. Soc., vol. 17, No. 7, pp. 1281-1290, (2006).
The International Search Report for International Application No. PCT/IL2011/050053, three pages, mailed on Nov. 27, 2012.
The International Search Report for International Application No. PCT/IL2011/050054, four pages, mailed on Mar. 1, 2013.
Chen et al., "Chemical constituents in Populus davidiana", Chinese Traditional and Herbal Drugs, vol. 37, No. 6, pp. 816-818, (2006). English Abstract on p. 816.
Lin, "The flavour component and antimicrobiol insecticidal functiond of Wasabi", China Condiment, vol. 1, No. 1, pp. 12-14 and 23, (2004). English Abstract on p. 12.
Tang et al., "Bioactivities and Application Research of Saponin from Pericarps of Sapindus mukorossi", Nat Prod Res Dev, vol. 19, pp. 562-565, (2007). English Abstract on p. 562.
Zhao et al., "Study on honeysuckle antimicrobial extraction and antimicrobial effect", Journal of Shaoyang College, vol. 14, No. 3, pp. 204-209, (2001). English Abstract on p. 209.

* cited by examiner

US 9,474,283 B2

FORMULATIONS COMPRISING SAPONINS AND USES THEREOF

FIELD OF THE INVENTION

This invention relates to formulations comprising saponins and uses thereof in a variety of cosmetic, therapeutic and preservative applications.

BACKGROUND OF THE INVENTION

As known in the art, saponins are compounds constructed of a triterpene or steroid moiety (aglycon or sapogenin) and one or two glycoside moieties (monodesmosides or bidesmosides, respectively). The aglycon carbon skeleton may be saturated or unsaturated and/or comprise a heteroatom such as nitrogen. The glycoside moiety contains sugars such as galactose, glucose, glucuronic acid, methylpentose, rhamnose and xylose.

The saponin family is known to have a wide range of biological activities such as antimicrobial, antiherbivore and/or cytotoxic activity and their role in nature is likely to be in defense against pathogens, pests and predators. In plants, saponins appear to act as pre-formed antimicrobial barriers to pathogen attack but can also function as suppressors of induced defense responses following hydrolysis [1].

Public concern about the safety of synthetic preservatives used in cosmetic and foods, especially regarding their accumulation and subsequent health effect, have driven health authorities to reduce the applied concentrations or even ban synthetic preservatives. Alternatives such as plant antimicrobial substances are in the focus of many researches, however due to low potency, narrow range and high prices, they are rarely used to replace synthetic preservatives.

The state of the art includes attempts to utilize naturally occurring compounds in cosmetic compositions. For example:

US 2011/0020302 [2] discloses a cosmetic composition comprising natural occurring ingredients having 0.1 to 20 w/w species of *Lonicera*.

WO 2000/072861 [3] discloses to a method of extraction bioactive substances such as saponins from plants by supercritical fluid extractions.

WO 1998/048768 [4] discloses a cosmetic composition comprising extracts of species of *Camellia* and *Lonicera* as possible additives.

US 2006/0018867 [5] discloses a cosmetic composition comprising polyorganosyloxane-containing epsilon polylysine compounds and an antimicrobial agent. *Lonicera japonica* extract is mentioned out of a very long list as an anti-inflammatory agent, an astringent, and as a tyrosinase inhibitor. Saponins are mentioned as antimicrobial agents and as pigmentation inhibitor. The publication also teaches optionally adding a saponin as a natural surfactant and/or a humectant.

WO 2009153800 [6] teaches extractions of saponins from *Sapindus trifoliatus*.

REFERENCES

[1] "The saponins—polar isoprenoids with important and diverse biological activities" A. Osbourn, et al., Nat. Prod. Rep., 2011, 28, 1261;
[2] US application no. 2011/0020302;
[3] WO 2000/072861;
[4] WO 1998/048768;
[5] US application no. 2006/0018867;
[6] WO 2009153800;
[7] U.S. Pat. No. 4,247,569;
[8] U.S. Pat. No. 2,996,540;
[9] US application no. 2010/183528.

SUMMARY OF THE INVENTION

The inventors of the invention have surprisingly found that compositions of at least one saponin material and an extract of at least one plant species of a genus selected from *Lonicera, Populus, Salix* and *Wasabia* or any mixture of extracts thereof exhibit biological activity, e.g., antimicrobial activity, which is superior to the activity demonstrated for each component individually and which is at least comparable and even superior to chemical alternatives known for a particular use.

In its first aspect, the invention provides a composition comprising at least one saponin material and an extract from at least one plant species of a genus selected from *Lonicera, Populus, Salix* and *Wasabia* or a mixture thereof.

As used herein, the "saponin material" is at least one naturally obtained saponin compound, as known in the art. When isolated from a natural source, the at least one saponin may be used in its substantially pure form (namely at least 85%, 87%, 92%, 95%, or 98% purity), or may be used as a saponin-containing extract isolated by a method known in the art or by a method of the invention, as disclosed herein.

In accordance with the present invention, the saponin-containing extract (herein referred to for the purpose of brevity as "saponin extract") contains at least between 0.2% and 95 wt % saponins, out of the total weight of the dry content of the extract. In some embodiments, the extract used in accordance with the present invention comprises between 0.2% and 99 wt % saponins out of the total weight of the dry content of the extract.

In some embodiments, the extract used in accordance with the present invention comprises between 10% and 80 wt % saponins out of the total weight of the dry content of the extract. In other embodiments, the extract used in accordance with the present invention comprises between 10% and 60 wt % saponins out of the total weight of the dry content of the extract. In further embodiments, the extract used in accordance with the present invention comprises between 10% and 50 wt % saponins out of the total weight of the dry content of the extract. In additional embodiments, the extract used in accordance with the present invention comprises between 10% and 40 wt % saponins out of the total weight of the dry content of the extract. In still additional embodiments, the extract used in accordance with the present invention comprises between 10% and 30 wt % saponins out of the total weight of the dry content of the extract.

In some embodiments, the extract used in accordance with the present invention comprises between 10% and 20 wt % saponins out of the total weight of the dry content of the extract.

In some embodiments, the extract used in accordance with the present invention comprises between 0.2% and 10 wt % saponins out of the total weight of the dry content of the extract.

The saponin-containing extract may be obtained from any natural source known to comprise saponins. Such natural source may be a plant source, some of which are detailed infra, and also from non-plant sources such as animal sources and marine organisms, such as starfish and sea cucumbers. In some embodiments of the invention, the saponins are extracted from a plant source, naturally grown or genetically modified to have high saponin content.

In some embodiments of the invention, the saponin material is obtained by extraction from a plant source by employing water, alcohol or a water/alcohol solution. In some embodiments, the alcohol is ethanol or methanol.

In some embodiments, the extraction is achieved by employing a water/alcohol solution. In some embodiments, the water/alcohol solution has a water:alcohol ratio of between 80:20 to 20:80. In further embodiments, the water/alcohol solution has a water:alcohol ratio of between 60:40 to 40:60. In further embodiments, the water/alcohol solution is 80:20 water/alcohol, 60:40 water/alcohol, 50:50 water/alcohol, 40:60 water/alcohol ratio or 20:80 water/alcohol.

The extraction time may vary without limitation from 1 to 8 hours, at or above room temperature (20° C.-30° C.), e.g., above 30° C., 40° C., 50° C. or 60° C. In some embodiments, the extraction is carried out at a temperature between 30° C. and 70° C.

In some embodiments, the saponin material is obtained from a plant source. The plant source may be selected from shikakai, soyabeans, beans, peas (*Pisum sativum*), lucerne, tea, spinach, sugar beet, quinoa, liquorice, sunflower, horse chestnut, ginseng, oats, capsicum peppers, aubergine, tomato seed, alliums, asparagus, yam, fenugreek, yucca and ginseng, lucerne, mung beans, *Bupleurum falcatum*, *Camellia oleifera*, *Camellia sinensis Desmodium adscendens*, *Gypsophila*, *Panax quinqufolius*, *Panax japonicas*, *Quillaja saponaria*, *Sapindus delavayi*, *Sapindus mukorossi*, *Sapindus marginatus*, *Sapindus saponaria*, *Sapindus trifoliatus*, *Saponaria officinalis*, *Styrax japonica*, and *Yucca schidigera* or any mixture thereof. Any part of the plant may be used for extracting the saponin material, including leaves, stems, roots, bulbs, blossom and fruit (including the skin, flesh and seed of the fruit).

In some embodiments, the saponin material is an extract of *Camellia sinensis*, *Camellia oleifera*, *Saponaria officinalis*, or *Sapindus mukorossi* or a mixture thereof.

In other embodiments, the saponin material is an extract of *Camellia oleifera*, or *Sapindus mukorossi* or a mixture thereof.

The saponin material obtained from a plant source, e.g., *Camellia oleifera*, and/or *Sapindus mukorossi*, may be extracted as disclosed hereinbelow. In some embodiments, the extraction process comprising: treating the plant source in a water/alcohol solution under conditions permitting extraction of the saponin material into the solution. The so-extracted saponin containing material may subsequently be purified by any means known in the art, including: filtration, centrifugation, re-crystallization, distillation, adsorption, chromatographic methods, fractionation, etc.

In some embodiments, the plant source is first dried and ground before being treated in the water/alcohol solution.

In some embodiments, the saponin material is extracted from a plant source following a method comprising:
1. treating the plant source in a 40:60 to 60:40 water:alcohol solution for a period of time and under conditions permitting extraction of the saponin material from said plant source into said solution, as defined hereinabove;
2. optionally, evaporating the saponin-containing solution to obtain a saponin-containing solid material; and
3. optionally, purifying said saponin-containing solid material.

In some embodiments, the plant source is one or both of *Camellia oleifera* and *Sapindus mukorossi*. In some embodiments, the plant source is *Sapindus mukorossi* and the saponin material is extracted from the nut shell. In other embodiments, the plant source is *Camellia oleifera* and in some embodiments the saponin material is extracted from the defatted seed meal of *Camellia oleifera*.

As stated above, the composition of the invention comprises at least one saponin material and an extract from at least one plant species of a genus selected from *Lonicera*, *Populus*, *Salix* and *Wasabia* or a mixture of extracts thereof. It should be understood that the extract may be an extract of more than one plant selected from *Lonicera*, *Populus*, *Salix* and *Wasabia* and that each plant may be selected from the same genus or from a different genus. It should be further that the present invention further contemplates composition comprising mixtures of extract, whether prepared and formulated individually or prepared in one-pot from a mixture of plant sources (plant parts).

The genus "*Lonicera*" contains a group of arching shrubs or twining vines in the family Caprifoliaceae that are commonly known as Honeysuckles. Known species include *Lonicera periclymenum* (European Honeysuckle or Woodbine), *Lonicera japonica* (Japanese Honeysuckle, White Honeysuckle, or Chinese Honeysuckle) and *Lonicera sempervirens* (Coral Honeysuckle, Trumpet Honeysuckle, or Woodbine Honeysuckle).

In some embodiments, the *Lonicera* extract is an extract of *Lonicera periclymenum* (European Honeysuckle or Woodbine), *Lonicera japonica* (Japanese Honeysuckle, White Honeysuckle, or Chinese Honeysuckle) and/or *Lonicera sempervirens* (Coral Honeysuckle, Trumpet Honeysuckle, or Woodbine Honeysuckle). In other embodiments, the *Lonicera* extract is an extract of *Lonicera japonica* (Japanese Honeysuckle, White Honeysuckle, or Chinese Honeysuckle).

The genus "*Populus*" comprises species of deciduous flowering plants in the family Salicaceae. Species of this genus include aspen (e.g., *Populus adenopoda*, *Populus alba*, *Populus grandidentata*, *Populus sieboldii*, *Populus tremula* and *Populus tremuloides*), and cottonwood (e.g., *Populus deltoids*, *Populus fremontii* and *Populus nigra*).

In some embodiments, the *Populus* extract is an extract of aspen (e.g., *Populus adenopoda*, *Populus alba*, *Populus grandidentata*, *Populus sieboldii*, *Populus tremula* and *Populus tremuloides*), and/or cottonwood (e.g., *Populus deltoids*, *Populus fremontii* and *Populus nigra*). In other embodiments, the *Populus* extract is an extract of aspen selected from *Populus adenopoda*, *Populus alba*, *Populus grandidentata*, *Populus sieboldii*, *Populus tremula* and *Populus tremuloides*. In other embodiments, the extract is of *Populus tremuloides*.

The genus "*Salix*" belonging to the Salicaceae family specifically includes the species *Salix herbacea*, *Salix babylonica*, *Salix alba*, *Salix x sepulcralis* (weeping willow), and also includes inter alia the species *Salix aegyptiaca*, *Salix alaxensis*, *Salix alba*, *Salix amplexicaulis*, *Salix amygdaloides*, *Salix ansoniana*, *Salix apennina*, *Salix apoda*, *Salix appendiculata*, *Salix arbuscula*, *Salix arctica*, *Salix argyracea*, *Salix arizonica*, *Salix armenorossica*, *Salix atrocinerea*, *Salix aurita*, *Salix babylonica*, *Salix balfouriana*, *Salix barclayi*, *Salix bebbiana*, *Salix bicolor*, *Salix bikouensis*, *Salix bonplandiana*, *Salix boothii*, *Salix brachycarpa*, *Salix breviserrata*, *Salix breweri*, *Salix burqinensis*, *Salix caesia*, *Salix calcicola*, *Salix calliantha*, *Salix canariensis*, *Salix candida*, *Salix cantabrica*, *Salix capensis*, *Salix capitata*, *Salix caprea*, *Salix capusii*, *Salix carmanica*, *Salix caroliniana*, *Salix caspica*, *Salix cavaleriei*, *Salix chaenomeloides*, *Salix cinerea*, *Salix cordata*, *Salix delnortensis*, *Salix discolor*, *Salix drummondiana*, *Salix eastwoodiae*,

*Salix eriocephala, Salix excelsa, Salix exigua, Salix fargesii, Salix floderusii, Salix fluviatilis, Salix foetida, Salix fragilis, Salix geyeriana, Salix gilgiana, Salix glabra, Salix glauca, Salix glaucosericea, Salix gooddingii, Salix gordejevii, Salix graciliglans, Salix gracilistyla, Salix hastata, Salix hegetschweileri, Salix helvetica, Salix herbacea, Salix hookeriana, Salix humboldtiana, Salix humilis, Salix hylematica, Salix integra, Salix irrorata, Salix japonica, Salix jejuna, Salix jepsonii, Salix jessoensis, Salix koreensis, Salix koriyanagi, Salix laevigata, Salix lanata, Salix lapponum, Salix lasiolepis, Salix lemmonii, Salix ligulifolia, Salix linearistipularis, Salix longiflora, Salix longistamina, Salix lucida, Salix lutea, Salix magnifica, Salix matsudana, Salix maximowiczii, Salix medwedewii, Salix melanopsis, Salix microstachya, Salix mielichhoferi, Salix miyabeana, Salix moupinensis, Salix mucronata, Salix muscina, Salix myricoides, Salix myrsinifolia, Salix myrsinites, Salix myrtilloides, Salix neowilsonii, Salix nigra, Salix nivalis, Salix orestera, Salix paraplesia, Salix pauciflora, Salix pedicellata, Salix pellita, Salix pentandra, Salix petiolaris, Salix phlebophylla, Salix phylicifolia, Salix planifolia, Salix polaris, Salix prolixa, Salix purpurea, Salix pyrenaica, Salix pyrifolia, Salix pyrolifolia, Salix rehderiana, Salix repens, Salix reptans, Salix reticulata, Salix retusa, Salix retusoides, Salix rorida, Salix rosmarinifolia, Salix sajanensis, Salix salviifolia, Salix schwerinii, Salix scouleriana, Salix sericea, Salix serissima, Salix serpyllifolia, Salix sessilifolia, Salix sitchensis, Salix siuzevii, Salix starkeana, Salix subopposita, Salix subserrata, Salix suchowensis, Salix sungkianica, Salix taxifolia, Salix tenuijulis, Salix tetrasperma, Salix triandra, Salix turanica, Salix turfacea, Salix udensis., Salix uva-ursi, Salix variegata, Salix vestita, Salix viminalis, Salix vulpina, Salix waldsteiniana, Salix wallichiana, Salix wilhelmsiana, Salix wilsonii, Salix yezoalpina.*

In some embodiments, the extract of a species belonging to the *Salix* genum is *Salix alba*. In some embodiments, the extract of a species belonging to the *Salix* genum is extracted from the leaves and in some embodiments it is extracted from the park of the plant.

The genus "*Wasabia*" belonging to the Brassicaceae family includes inter alia the species *Wasabia japonica, Wasabia koreana, Wasabia tetsuigi, Wasabia tenuis, Wasabia bracteata, Wasabia okinosimensis, Wasabia pungens, Wasabia thibeticum* and *Wasabia yunnanensis*. In some embodiments, the *Wasabia* extract is an extract of *Wasabia japonica, Wasabia koreana, Wasabia tetsuigi, Wasabia tenuis, Wasabia bracteata, Wasabia okinosimensis, Wasabia pungens, Wasabia thibeticum* and/or *Wasabia yunnanensis*. In other embodiments, the *Wasabia* extract is an extract of *Wasabia japonica*.

The extract from the above identified plant sources may be obtained from any part of the plant, including leaves, stems, roots, bulbs, blossom and fruit (including the skin, flesh and seed of the fruit). In some embodiments, the extracts are obtained from the nut of *Sapindus mukorossi*, the seed meal of *Camellia oleifera*, the flower and buds of *Lonicera japonica*, the root of *Wasabia japonica*, the bark of *Populus tremuloides* or a combination thereof.

In other embodiments, each of the plant extracts is obtained commercially.

In some embodiments, the composition of the invention comprises a saponin material and at least one extract selected from *Lonicera japonica, Populus tremuloides, Salix alba* and *Wasabia japonica*.

Generally, in the compositions of the invention, the weight-to-weight ratio (wt/wt) between the saponin material and each of the extracts of a species belonging to the *Lonicera, Populus, Salix* or *Wasabia* genus may independently range between 1:100 to 100:1 (saponin material: species extract). In some embodiments, the weight-to-weight ratio between the saponin material and each of the extracts is independently about 1:10 to 1:100. In some embodiments, the weight-to-weight ratio between the saponin material and each of the extracts is independently about 1:100, 1:90, 1:80, 1:70, 1:60, 1:50, 1:40, 1:30, 1:20, 1:15, 1:10, 1:9, 1:8, 1:7, 1:6, 1:5, 1:4, 1:3, 1:2, 1:1, 2:1; 3:1, 4:1, 5:1, 6:1, 7:1, 8:1, 9:1, 10:1, 20:1, 30:1, 40:1, 50:1, 60:1, 70:1, 80:1, 90:1 or about 100:1.

In some embodiments, the weight of the saponin material may be in excess as compared to other active components in the final composition.

In some embodiment, the amount of the saponin material of the total weight of the solid materials in the composition is in the range of 0.33-99 wt %.

In some embodiments, the amount of the saponin material of the total weight of the composition is in the range of 1-30 wt %.

In another aspect of the present invention, there is provided a composition comprising at least one saponin material, a salicylate and/or salicine (2-(hydroxymethyl)phenyl-β-D-glucopyrano side).

As used herein, "salicylate" refers to a derivative of salicylic acid (2-hydroxybenzenecarboxylic acid), which may be synthetic or naturally-obtained. The term encompasses the salt form (base addition salt) of salicylic acid as well as esters and amides of salicylic acid. The salts of salicylic acid may be metal or amine salts, derived from alkali and alkaline earth metals or organic amines and ammonia. According to some embodiments, the composition comprises salicylate esters such as methyl salicylate, ethyl salicylate, propyl salicylate, butyl salicylate, pentyl salicylate, hexyl salicylate, cyclohexyl salicylate, benzyl salicylate and others.

In some embodiments, the at least one salicylate is derivable from at least one plant source. In further embodiments, the plant source is at least one plant species of a genus selected from *Lonicera, Populus, Salix* and *Wasabia* or a mixture thereof, as defined hereinabove.

In some embodiments, the at least one salicylate is derivable from a plant selected from *Betula lenta* (sweet birch), *Betula pendula* (white birch), *Filipendula ulmaria* (meadowsweet), *Gaultheria procumbens* (wintergreen), *Populus balsamifera* (balsam poplar), *Populus nigra* (black poplar), *Populus candicans* (balm of gilead), *Salix alba* (white willow) and *Viburnum prunifolium* (black haw).

In some embodiments, the composition comprises a saponin material and at least one of *Lonicera japonica* extract, *Wasabia japonica* extract and/or *Populus tremuloides*, and salyciate.

In some embodiments, the composition of the invention further comprises onr or more of arbutin (obtainable from bearberry), leontopodic acid (obtainable by extraction from edelweiss) and chlorogenic acid (obtainable by extraction from green tea, apple, potato, *lonicera* and other sources).

The compositions of the invention can be prepared by any commonly used method for preparing a composition of materials. For example the components of the composition may be added as solids and mixed together, or one of the components may be added to the other in the form of a solution which may, if desired be evaporated or lyophilized after mixing for obtaining a homogeneous solution.

As will be further demonstrated below, the compositions of the invention exhibit antimicrobial, non-tearing, surface-active, foaming, cleansing, anti-oxidizing, humectating, and softening properties which render the compositions suitable for a variety of applications in the fields of, e.g., cosmetics, therapeutics, foodstuffs and as material preservation. The composition of the invention may thus be formulated into a variety of formulations, such as a cosmetic formulation, a therapeutic formulation, an antimicrobial formulation, a food additive formulation and a preservative formulation. Each of the aforementioned formulations may further comprise an excipient, diluents, or carrier suitable for the particular application, together with at least one additional additive as disclosed herein.

In another of its aspects, the invention provides a cosmetic or cleansing formulation comprising at least one saponin material and an extract from at least one plant species of a genus selected from *Lonicera, Populus, Salix* and *Wasabia* or a mixture of extracts thereof, as defined in the various embodiments hereinabove.

The cosmetic/cleansing formulations according to the invention are typically formulated in a form adapted for topical application comprising a cosmetically or dermatologically acceptable medium, namely a medium which is suitable for application onto the skin of a subject (human or non-human). The medium may be in the form of aqueous or hydroalcoholic solution, an oil-in-water or water-in-oil emulsion, a microemulsion, aqueous or anhydrous gels, serum, or else a dispersion of vesicles, a patch, cream, spray, salve, ointment, lotion, gel, solution, suspension, or any other known cosmetically acceptable form. The formulation may alternatively be formulated for application to the human skin, hair, eyelashes, eyebrows, or nails.

In addition, the formulation may contain other standard additives such as an emollient, moisturizer, thickener, emulsifier, neutralizer, coloring agent, a fragrance, absorber or filter, preservative and/or gelling agent such as those described below, filler such as nylon, a sun screen agent, electrolytes, proteins, antioxidants and chelating agents.

The formulation may also further comprise at least one active ingredient such as peptide active ingredients, vegetable extracts, anti-age agents, anti-wrinkle agents, soothing agents, radical scavengers, UV absorbing agents, agents stimulating the synthesis of dermal macromolecules or the energy metabolism, hydrating agents, anti-bacterial agents, anti-fungal agents, anti-inflammatory agents, anesthetic agents, agents modulating cutaneous differentiation, pigmentation or de-pigmentation, agents stimulating nail or hair growth.

In some embodiments, each of the aforementioned additives/active ingredients is generally present in an amount of between about 0.1 to 30 wt % of the total weight of the formulation.

Suitable emollients for use in a cosmetic/cleansing formulation according to the invention include, for example, optionally hydroxy-substituted $C_8$-$C_{50}$ unsaturated fatty acids and esters thereof, $C_1$-$C_{24}$ esters of $C_8$-$C_{30}$ saturated fatty acids such as isopropyl myristate, cetyl palmitate and octyldodecylmyristate (Wickenol 142), beeswax, saturated and unsaturated fatty alcohols such as behenyl alcohol and cetyl alcohol, hydrocarbons such as mineral oils, petrolatum, squalane, fatty sorbitan esters, lanolin and lanolin derivatives, such as lanolin alcohol ethoxylated, hydroxylated and acetylated lanolins, cholesterol and derivatives thereof, animal and vegetable triglycerides such as almond oil, peanut oil, wheat germ oil, linseed oil, jojoba oil, oil of apricot pits, walnuts, palm nuts, pistachio nuts, sesame seeds, rapeseed, cade oil, corn oil, peach pit oil, poppy seed oil, pine oil, castor oil, soybean oil, avocado oil, safflower oil, coconut oil, hazelnut oil, olive oil, grape seed oil, and sunflower seed oil and $C_1$-$C_{24}$ esters of dimer and trimer acids such as diisopropyl dimerate, diisostearylmalate, diisostearyldimerate and triisostearyltrimerate.

In some embodiments, the emollients used in a formulation according to the invention include isocetyl alcohol, octyl palmitate, isostearyl neopentanoate and isocetyl stearyl stearate, natural or synthetic oils selected from mineral, vegetable, and animal oils, fats and waxes, fatty acid esters, fatty alcohols, alkylene glycol and polyalkylene glycol ethers and esters, fatty acids and mixtures thereof.

The emollients may be used independently or in mixtures and may be present in the composition of the present invention in an amount from about 1 to about 98% by weight, and in some embodiments are present in an amount from about 5% to about 15% by weight of the total formulation.

Suitable emulsifiers for use in a cosmetic/cleansing formulation according to the present invention include glyceryl stearate and laureth 23, PEG 20 stearate, and mink-amidopropyl dimethyl 2-hydroxyethylammonium chloride.

Typical moisturizers are glycerin, petrolatum and maleated vegetable oil.

The formulation of the invention may also contain a hydrophilic gelling agent. In some embodiments, the gelling agent is selected amongst such having a viscosity (1% aqueous solution, 20° C., Brookfield RVT) of at least about 4000 mPa. According to other embodiments, the gelling agent has a viscosity of about 10,000 mPa or at least 50,000 mPa.

In other embodiments, the hydrophilic gelling agents are selected from water-soluble or colloidal water-soluble polymers, such as cellulose ethers (e.g., hydroxyethyl cellulose, methyl cellulose, hydroxypropylmethyl cellulose), polyvinylalcohol, polyquaternium-10, guar gum, hydroxypropyl guar gum, xanthan gum, Aloe vera gel, amla, carrageenan, oat flour, starch (from corn rice or other plants), gelatin (porcine skin), ghatty gum, gum Arabic, inulin (from chicory), Konjac gum, locust bean gum, marshmallow root, pectin, quinoa extract, red alga, solagum and tragacanth gum (TG).

In further embodiments, the hydrophilic gelling agents are selected amongst acrylic acid/ethyl acrylate copolymers and the carboxyvinyl polymers sold by the B.F. Goodrich Company under the trademark of Carbopol resins. These resins consist essentially of a colloidal water-soluble polyalkenyl polyether crosslinked polymer of acrylic acid crosslinked with from 0.75% to 2.00% of a crosslinking agent such as polyallyl sucrose or polyallyl pentaerythritol. Examples include Carbopol 934, Carbopol 940, Carbopol 950, Carbopol 980, Carbopol 951 and Carbopol 981. Carbopol 934 is a water-soluble polymer of acrylic acid crosslinked with about 1 of polyallyl ether of sucrose having an average of about 5.8 allyl groups for each sucrose molecule. Also suitable for use herein are hydrophobically-modified crosslinked polymers of acrylic acid having amphipathic properties available under the Trade Name Carbopol 1382, Carbopol 1342 and Pemulen TR-1. A combination of the polyalkenyl polyether cross-linked acrylic acid polymer and the hydrophobically modified crosslinked acrylic acid polymer is also suitable for use herein.

Other suitable gelling agents suitable for use herein are oleogels such as trihydroxystearin and aluminum magnesium hydroxy stearate.

In some embodiments, the gelling agent is present in the cosmetic/cleansing formulation in an amount from about 0.01% to about 10% of the total weight of the formulation. In some embodiments, the formulation comprises a hydrophilic gelling agent in an amount between about 0.02% to about 2%. In other embodiments, the amount of the gelling agent is from about 0.02% to about 0.5%.

The cosmetic/cleansing formulation may also comprise a thickener, such as crosslinked maleic anhydride-alkyl methylvinylethers, and copolymers, commercially available as Stabilizes QM (International Specialty Products (ISP)), Carbomer, natural gums, highly crosslinked polymethacrylate copolymer, such as Microspongess 5647, which take the form of generally spherical particles of crosslinked hydrophobic polymer having a pore size of from about 0.01 to about 0.05 μm and a surface area of 200-300 m$^2$/g.

Neutralizing agents suitable for use in a cosmetic/cleansing formulation of the invention include neutralizing acidic group containing hydrophilic gelling agents, as listed herein, sodium hydroxide, potassium hydroxide, ammonium hydroxide, monoethanolamine, diethanolamine and triethanolamine and aminomethyl propanol.

In some embodiments, the cosmetic/cleansing formulation comprises one or more ultraviolet absorbing agents. Ultraviolet absorbing agents, often described as sun screening agents, may be present in a concentration between about 1% and about 25% by weight, based on the total weight of composition. According to some embodiments of the invention, the UV absorbing agent constitutes between about 2% and 15% by weight. According to other embodiments, the UV absorbing agent constitutes between about 4% and about 10% by weight. Non-limiting examples of ultraviolet absorbing agents include benzophenone-3, benzophenone-4, octyl dimethyl PABA (Padimate 0), octyl methoxy cinnamate, octyl salicylate, octocrylene, p-methylbenzylidene camphor, butyl methoxy dibenzoyl methane (Parsol 1789), titanium dioxide, zinc oxide and mixtures thereof.

The cosmetic/cleansing formulation of the invention may be used in treating or preventing formation of wrinkles, skin imperfections, fine lines, chapped skin, enlarged pores, losses in firmness, discoloration, aged areas, keratosis, losses in collagen, and other changes to the dermis and epidermis.

In a further aspect, the invention provides an antimicrobial formulation comprising at least one saponin material and at least one extract from a plant species of a genus selected from *Lonicera, Populus, Salix* and *Wasabia* or a mixture of extracts thereof, as defined herein.

The antimicrobial formulation of the invention is effective in reducing or eliminating a microorganism population or a biofilm of such microorganisms. As demonstrated herein, the formulations of the invention provide instant and persistent antimicrobial activity against a wide spectrum of microorganisms and specifically against a broad spectrum of bacteria. The term "microorganism" relates herein to a single cell (unicellular), cell clusters, or no cell (acellular) organism such as bacteria, fungi, yeast, mold, archaea, protists, viruses and algae.

In some embodiments, the microorganism is a bacteria, being selected, in some embodiments from *Bordetella pertussis, Borrelia burgdorferi, Brucella abortus, Brucella canis, Brucella melitensis, Brucella suis, Campylobacter jejuni, Chlamydia pneumonia, Chlamydia psittaci, Chlamydia trachomatis, Clostridium botulinum, Clostridium difficile, Clostridium perfringens, Clostridium tetani, Corynebacterium diphtheria, Enterococcus faecalis, Enterococcus faecium, Escherichia coli (E. coli), Enterotoxigenic Escherichia coli* (ETEC), *Enteropathogenic E. coli, Francisella tularensis, Haemophilus influenza, Helicobacter pylori, Legionella pneumophila, Leptospira interrogans, Listeria monocytogenes, Mycobacterium leprae, Mycobacterium tuberculosis, Mycoplasma pneumonia, Neisseria gonorrhoeae, Neisseria meningitidis, Pseudomonas aeruginosa, Rickettsia rickettsii, Salmonella typhi, Salmonella typhimurium, Shigella sonnei, Staphylococcus epidermidis, Staphylococcus saprophyticus, Streptococcus agalactiae, Streptococcus mutans Streptococcus pneumonia, Streptococcus pyogenes, Treponema pallidum, Vibrio cholera, Vibrio harveyi* and *Yersinia pestis*.

In some embodiments, the microorganism is a fungus, selected in some embodiments from *Absidia corymbifera, Ajellomyces capsulatus, Ajellomyces dermatitidis, Arthroderma benhamiae, Arthroderma fulvum, Arthroderma gypseum, Arthroderma incurvatum, Arthroderma otae, Arthroderma vanbreuseghemii, Aspergillus flavus, Aspergillus fumigates, Aspergillus niger, Blastomyces dermatitidis, Candida albicans, Candida albicans* var. *stellatoidea, Candida dublinensis, Candida glabrata, Candida guilliermondii, Candida krusei, Candida parapsilosis, Candida pelliculosa, Candida tropicalis, Cladophialophora carrionii, Coccidioides immitis, Cryptococcus neoformans, Cunninghamella* sp., *Epidermophyton floccosum, Exophiala dermatitidis, Filobasidiella neoformans, Fonsecaea pedrosoi, Geotrichum candidum, Histoplasma capsulatum, Hortaea werneckii, Issatschenkia orientalis, Madurella grisae, Malassezia furfur, Malassezia furfur complex, Malassezia globosa, Malassezia obtuse, Malassezia pachydermatis, Malassezia restricta, Malassezia slooffiae, Malassezia sympodialis, Microsporum canis, Microsporum fulvum, Microsporum gypseum, Microsporum gypseum complex, Microsporum gypseum, Mucor circinelloides, Nectria haematococca, Paecilomyces variotii, Paracoccidioides brasiliensis, Penicillium marneffei, Phialophora verrucosa, Pichia anomala, Pichia guilliermondii, Pneumocystis jirovecii, Pseudallescheria boydii, Rhizopus oryzae, Rodotorula rubra, Saccharomyces cerevisiae, Scedosporium apiospermum, Schizophyllum commune, Sporothrix schenckii, Stachybotrys chartarum, Trichophyton mentagrophytes, Trichophyton mentagrophytes complex, Trichophyton mentagrophytes, Trichophyton mentagrophytes, Trichophyton rubrum, Trichophyton tonsurans, Trichophyton verrucosum, Trichophyton violaceum, Trichosporon asahii, Trichosporon cutaneum, Trichosporon cutaneum complex, Trichosporon inkin* and *Trichosporon mucoides*.

In some embodiments, the microorganism is yeast, being selected, in some embodiments, from *Candida albicans, Candida albicans* var. *stellatoidea, Candida dublinensis, Candida glabrata, Candida guilliermondii, Candida krusei, Candida parapsilosis, Candida pelliculosa, Candida tropicalis, Cryptococcus neoformans, Filobasidiella neoformans, Geotrichum candidum, Issatschenkia orientalis, Malassezia furfur, Malassezia pachydermatis, Pichia anomala, Pichia guilliermondii, Pneumocystis jirovecii, Rodotorula rubra, Trichosporon asahii, Trichosporon cutaneum, Trichosporon inkin* and *Trichosporon mucoides*.

In some embodiments, the microorganism is mold, being selected, in some embodiments, from *Absidia corymbifera, Arthroderma benhamiae, Arthroderma fulvum, Arthroderma gypseum, Arthroderma incurvatum, Arthroderma otae, Arthroderma vanbreuseghemii, Aspergillus flavus, Aspergillus fumigates, Aspergillus niger, Cladophialophora carrionii, Coccidioides immitis, Epidermophyton floccosum, Exophiala dermatitidis, Fonsecaea pedrosoi, Hortaea werneckii, Madurella grisae, Microsporum canis, Microsporum fulvum, Microsporum gypseum, Microsporum gypseum, Microsporum gypseum, Mucor circinelloides, Nectria haematococca, Paecilomyces variotii, Paracoccidioides brasiliensis, Penicillium marneffei, Pseudallescheria boydii,*

*Rhizopus oryzae, Scedosporium apiospermum, Schizophyllum commune, Sporothrix schenckii, Stachybotrys chartarum, Trichophyton mentagrophytes complex, Trichophyton mentagrophytes, Trichophyton mentagrophytes, Trichophyton rubrum, Trichophyton tonsurans, Trichophyton verrucosum* and *Trichophyton violaceum.*

According to some embodiments of the invention, the antimicrobial formulations of the invention are effective against bacteria such as *Escherichia coli (E. Coli), Salmonella, Staphylococcus, Saccharomyces, Staphylococcus aureus, Pseudomonas aeruginosa, Candida albicans, A. niger* as exhibited by the below provided antimicrobial effectiveness testing.

In some embodiments, the antimicrobial formulations of the invention are effective in reducing, inhibiting eliminating or preventing the growth of *Staphylococcus, E. coli* and *salmonella.*

In some embodiments, the antimicrobial formulations of the invention are effective in reducing, inhibiting eliminating or preventing the growth of *Streptococcus mutans* and *Vibrio harveyi.*

In a further aspect, the invention provides a therapeutic formulation (pharmaceutical composition) comprising at least one saponin material and at least one extract from a plant species of a genus selected from *Lonicera, Populus, Salix* and *Wasabia* or a mixture of extracts thereof, as defined herein.

The pharmaceutical formulation of the invention may be effective in the treatment and/or prevention of a variety of diseases and disorders. As demonstrated hereinbelow, the formulations of the invention provide instant and persistent antimicrobial activity against a wide spectrum of microorganisms, as defined herein. In some embodiments, the disease or disorder to be treated is associated with bacterial infection, fungal infection or viral infection.

In some embodiments, the pharmaceutical composition of the invention is used in the treatment or prevention of a disease or disorder associated with a bacterial infection, wherein said bacterial infection is caused by a bacteria selected, without limitation, from *Bordetella pertussis, Borrelia burgdorferi, Brucella abortus, Brucella canis, Brucella melitensis, Brucella suis, Campylobacter jejuni, Chlamydia pneumonia, Chlamydia psittaci, Chlamydia trachomatis, Clostridium botulinum, Clostridium difficile, Clostridium perfringens, Clostridium tetani, Corynebacterium diphtheria, Enterococcus faecalis, Enterococcus faecium, Escherichia coli (E. coli), Enterotoxigenic Escherichia coli (ETEC), Enteropathogenic E. coli, Francisella tularensis, Haemophilus influenza, Helicobacter pylori, Lactobacilli, Legionella pneumophila, Leptospira interrogans, Listeria monocytogenes, Mycobacterium leprae, Mycobacterium tuberculosis, Mycoplasma pneumonia, Neisseria gonorrhoeae, Neisseria meningitidis, Plasmodium falciparum, Plasmodium knowlesi, Plasmodium sp., Pseudomonas aeruginosa, Rickettsia rickettsii, Saccharo yces cerevisiae, Salmonella typhi, Salmonella typhimurium, Shigella sonnei, Staphylococcus aureus, Staphylococcus epidermidis, Staphylococcus hemolyticus, Staphylococcus saprophyticus, Streptococcus agalactiae, Streptococcus mutans Streptococcus pneumonia, Streptococcus pyogenes, Treponema pallidum, Vibrio cholera, Vibrio harveyi* and *Yersinia pestis.*

Non-limiting examples of disease or disorder associated with a bacterial infection include lyme disease, brucellosis, acute enteritis, psittacosis, nongonococcal urethritis (NGU), trachoma, inclusion conjunctivitis of the newborn (ICN), lymphogranuloma venereum (LGV), botulism, pseudomembranous colitis, gas gangrene, acute food poisoning, anaerobic cellulitis, tetanus, diphtheria, nosocomial infections, urinary tract infections (UTI), diarrhea, meningitis, meningitis in infants, hemorrhagic colitis, hemolytic-uremic syndrome, tularemia, upper respiratory tract infections, pneumonia, mycoplasma pneumonia, secondary pneumonia, bronchitis, peptic ulcer, legionnaire's disease, gastric B-cell lymphoma, pontiac fever, leptospirosis, listeriosis, leprosy (Hansens disease), tuberculosis, gonorrhea, ophthalmia neonatorum, meningococcal disease, Waterhouse-Friderichsen, localized infection (of eye, ear, skin, urinary, respiratory), gastrointestinal tract infection, central nervous system infection, systemic infection with bacteremia, bone and joint infections, endocarditis, typhoid fever type salmonellosis, dysentery, colitis, salmonellosis with gastroenteritis and enterocolitis, bacillary dysentery/shigellosis, Streptococcal pharyngitis, Scarlet fever, rheumatic fever, impetigo and erysipelas, puerperal fever, necrotizing fasciitis, syphilis, congenital syphilis and cholera.

In some embodiments, the bacterial disease or disorder is associated with *Staphylococcus* or *Escherichia coli (E. coli)* or *salmonella* infections; the disease or disorder being selected from:

*Staphylococcus*: coagulase-positive staphylococcal infections such as Localized skin infections, diffuse skin infection (impetigo), deep and localized infections, acute infective endocarditis, septicemia, necrotizing pneumonia, toxinoses, toxic shock syndrome, staphylococcal food poisoning, infections of implanted prostheses e.g., heart valves and catheters and cystitis in women;

*E. coli*: urinary tract infections (UTI), diarrhea, meningitis in infants, traveler's diarrhea, hemorrhagic colitis and hemolytic-uremic syndrome;

*Salmonella*: typhoid fever type salmonellosis, dysentery, colitis, salmonellosis, e.g., with gastroenteritis and enterocolitis.

In some embodiments, the pharmaceutical composition of the invention is used in the treatment or prevention of a disease or disorder associated with a fungal infection, wherein said fungal infection is caused by a fungus selected, without limitation, from *Absidia corymbifera, Ajellomyces capsulatus, Ajellomyces dermatitidis, Arthroderma benhamiae, Arthroderma fulvum, Arthroderma gypseum, Arthroderma incurvatum, Arthroderma otae, Arthroderma vanbreuseghemii, Aspergillus flavus, Aspergillus fumigates, Aspergillus niger, Blastomyces dermatitidis, Candida albicans, Candida albicans var. stellatoidea, Candida dublinensis, Candida glabrata, Candida guilliermondii, Candida krusei, Candida parapsilosis, Candida pelliculosa, Candida tropicalis, Cladophialophora carrionii, Coccidioides immitis, Cryptococcus neoformans, Cunninghamella sp., Epidermophyton floccosum, Exophiala dermatitidis, Filobasidiella neoformans, Fonsecaea pedrosoi, Geotrichum candidum, Histoplasma capsulatum, Hortaea werneckii, Issatschenkia orientalis, Madurella grisae, Malassezia furfur, Malassezia furfur complex, Malassezia globosa, Malassezia obtuse, Malassezia pachydermatis, Malassezia restricta, Malassezia slooffiae, Malassezia sympodialis, Microsporum canis, Microsporum fulvum, Microsporum gypseum, Microsporum gypseum complex, Microsporum gypseum, Mucor circinelloides, Nectria haematococca, Paecilomyces variotii, Paracoccidioides brasiliensis, Penicillium marneffei, Phialophora verrucosa, Pichia anomala, Pichia guilliermondii, Pneumocystis jirovecii, Pseudallescheria boydii, Rhizopus oryzae, Rodotorula rubra, Scedosporium apiospermum, Schizophyllum commune, Sporothrix schenckii, Stachybotrys chartarum, Trichophyton mentagrophytes, Trichophyton mentagrophytes complex, Trichophyton men-* tagrophytes, *Trichophyton mentagrophytes, Trichophyton rubrum, Trichophyton tonsurans, Trichophyton verrucosum, Trichophyton violaceum, Trichosporon asahii, Trichosporon cutaneum, Trichosporon cutaneum complex, Trichosporon inkin* and *Trichosporon mucoides*.

In some embodiments, the pathogen is yeast. The yeast causing disease or disorder may be selected from *Candida albicans, Candida albicans* var. *stellatoidea, Candida dublinensis, Candida glabrata, Candida guilliermondii, Candida krusei, Candida parapsilosis, Candida pelliculosa, Candida tropicalis, Cryptococcus neoformans, Filobasidiella neoformans, Geotrichum candidum, Issatschenkia orientalis, Malassezia furfur, Malassezia pachydermatis, Pichia anomala, Pichia guilliermondii, Pneumocystis jirovecii, Rodotorula rubra, Saccharomyces cerevisiae. Trichosporon asahii, Trichosporon cutaneum, Trichosporon inkin* and *Trichosporon mucoides*.

In some embodiments, the pathogen is mold. The mold causing disease or disorder is selected from *Absidia corymbifera, Arthroderma benhamiae, Arthroderma fulvum, Arthroderma gypseum, Arthroderma incurvatum, Arthroderma otae, Arthroderma vanbreuseghemii, Aspergillus flavus, Aspergillus fumigates, Aspergillus niger, Cladophialophora carrionii, Coccidioides immitis, Epidermophyton floccosum, Exophiala dermatitidis, Fonsecaea pedrosoi, Hortaea werneckii, Madurella grisae, Microsporum canis, Microsporum fulvum, Microsporum gypseum, Microsporum gypseum, Microsporum gypseum, Mucor circinelloides, Nectria haematococca, Paecilomyces variotii, Paracoccidioides brasiliensis, Penicillium marneffei, Pseudallescheria boydii, Rhizopus oryzae, Scedosporium apiospermum, Schizophyllum commune, Sporothrix schenckii, Stachybotrys chartarum, Trichophyton mentagrophytes complex, Trichophyton mentagrophytes, Trichophyton mentagrophytes, Trichophyton rubrum, Trichophyton tonsurans, Trichophyton verrucosum* and *Trichophyton violaceum*.

According to some embodiments of the invention, the formulations of the invention are effective against bacteria such as *E. Coli, Salmonella, Staphylococcus, Saccharomyces, S. aureus, P. aeruginosa, C. albicans, A. niger* as exhibited by the below provided antimicrobial effectiveness testing. The combination of saponins with an extract of the genus *Lonicera, Populus, Salix Wasabia* or a mixture thereof exhibits potency which is effective against these types of bacteria at concentrations which are much lower than what would be required if each one of the components was used individually. For example, where an exemplary formulation according to the invention comprises 10% soap, 0.2% Aspen bark extract (*Populus tremuloides*) and 2% of the saponin material, a reduction in *Salmonella* total counts by 6 logs even after just 72 h of incubation has been demonstrated.

According to some embodiments the formulation effectively acts as an antimicrobial agent against *E. coli, S. aureus, P. aeruginosa, C. albicans* and *Aspergillus niger*.

According to some embodiments the formulation effectively acts as an antimicrobial agent against *E. coli*.

According to some embodiments the formulation effectively acts as an antimicrobial agent *S. aureus*.

According to some embodiments the formulation effectively acts as an antimicrobial agent against *P. aeruginosa*.

According to some embodiments the formulation effectively acts as an antimicrobial agent against *C. albicans*.

According to some embodiments the formulation effectively acts as an antimicrobial agent against *Aspergillus niger*.

According to some embodiments the formulation effectively acts as an antimicrobial agent against *Streptococcus mutans* and *Vibrio harveyi*.

According to some embodiments the formulation effectively acts as an antimicrobial agent against *Streptococcus mutans*.

According to some embodiments the formulation effectively acts as an antimicrobial agent against *Vibrio harveyi*.

The pharmaceutical composition may be adapted for administration by a variety of routes including topical, oral, rectal, vaginal, transdermal, subcutaneous, intravenous, intramuscular, eye drops and intranasal. Such pharmaceutical composition is prepared in a manner well known in the pharmaceutical art. In making the pharmaceutical composition of the invention, the aforementioned components are usually mixed with an excipient, diluted by an excipient or enclosed within such a carrier which can be manipulated to the desired form. Based on the particular mode of administration, the pharmaceutical composition may be formulated into tablets, pills, capsules, sachets, granules, powders, chewing gum, suspensions, emulsions and solutions.

The pharmaceutically acceptable carriers, for example, vehicles, adjuvants, excipients, or diluents, are well-known to those who are skilled in the art and are readily available to the public. It is preferred that the pharmaceutically acceptable carrier be one which is chemically inert to the active formulation and each of its components and one which has no detrimental side effects or toxicity under the conditions of use.

The choice of carrier will be determined in part by the particular formulation of the invention, as well as by the particular method used to administer the composition. Accordingly, there is a wide variety of suitable formulations of the pharmaceutical composition of the present invention.

Formulations suitable for oral administration can consist of (a) liquid solutions, such as an effective amount of the compound, or composition comprising same, dissolved in diluents, such as water, saline, or juice (e.g. orange juice); (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, talc, magnesium stearate, calcium stearate, zinc stearate, stearic acid, and other excipients, colorants, diluents, buffering agents, disintegrating agents, moistening agents, preservatives, flavoring agents, and pharmacologically compatible carriers. Lozenge forms can comprise the active ingredient in a flavor, usually sucrose and acacia or tragacanth, as well as pastilles comprising the active formulation in an inert base, such as gelatin and glycerin, or sucrose and acacia, emulsions, gels, and the like containing, in addition to the active formulation, such carriers as are known in the art.

The formulations of the present invention, alone or in combination with other suitable components, e.g., active or non-active additives/ingredients can be made into aerosol formulations to be administered via inhalation. These aerosol formulations can be placed into pressurized acceptable propellants, such as dichlorodifluoromethane, propane, nitrogen, and the like. They also may be formulated as pharmaceuticals for non-pressured preparations, such as in a nebulizer or an atomizer Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that include suspending agents, solubilizers, thickening agents, stabilizers, and preservatives. The formulation can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol, glycerol ketals, such as 2,2-dimethyl-1,3-dioxolane-4-methanol, ethers, such as poly(ethyleneglycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical additives.

Oils, which can be used in parenteral formulations, include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters. Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxy-ethylenepolypropylene copolymers, (d) amphoteric detergents such as, for example, alkyl-β-aminopriopionates, and 2-alkyl-imidazoline quaternary ammonium salts, and (3) mixtures thereof.

In order to minimize or eliminate irritation at the site of injection, such compositions may contain one or more nonionic surfactants having a hydrophile-lipophile balance (HLB) of from about 12 to about 17. The quantity of surfactant in such formulations ranges from about 5 to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described.

The active formulation is effective over a wide dosage range and may generally be administered in a pharmaceutically effective amount. It should be understood, however, that the amount of the formulation or each component thereof to be administered, will be determined by a physician, in the light of the relevant circumstances, including the condition to be treated, the chosen route of administration, the actual formulation, the age, weight, and response of the individual patient, the severity of the patient's symptoms, and the like.

In another aspect of the invention, there is provided the use of a formulation of the invention as herein defined, for the preparation of a pharmaceutical composition for treating or preventing a disease or disorder in a mammal (human or non-human).

In some embodiments, the disease or disorder is associated with a bacteria, virus, fungus, yeast or mold.

As used herein, the term "treatment" or any lingual variation thereof, refers to the administering of a therapeutic amount of the composition of the present invention which is effective to ameliorate undesired symptoms associated with a disease, to prevent the manifestation of such symptoms before they occur, to slow down the progression of the disease, slow down the deterioration of symptoms, to enhance the onset of remission period, slow down the irreversible damage caused in the progressive chronic stage of the disease, to delay the onset of said progressive stage, to lessen the severity or cure the disease, to improve survival rate or more rapid recovery, or to prevent the disease form occurring or a combination of two or more of the above. The "effective amount" for purposes disclosed herein is determined by such considerations as may be known in the art. The amount must be effective to achieve the desired therapeutic effect as described above, depending, inter alia, on the type and severity of the disease to be treated and the treatment regime. The effective amount is typically determined in appropriately designed clinical trials (dose range studies) and the person versed in the art will know how to properly conduct such trials in order to determine the effective amount. As generally known, an effective amount depends on a variety of factors including the affinity of the ligand to the receptor, its distribution profile within the body, a variety of pharmacological parameters such as half life in the body, on undesired side effects, if any, on factors such as age and gender, etc.

In yet another aspect, the invention provides a preservative formulation comprising at least one saponin material and an extract from at least one plant species of a genus selected from *Lonicera, Populus, Salix* and *Wasabia* or a mixture of extracts thereof, as defined herein.

The preservative formulation of the invention may be used to reduce, inhibit or completely eliminate pathogen population in a variety of consumer products, such as personal care products, industrial products, food products, therapeutics, and others. As demonstrated herein, the formulation of the invention may be used to replace currently available chemicals which are used as preservatives, some of which known as toxic to humans and animals, or at reduce their concentration in such products for human or animal use. The preservative formulation may be added to any such product, such as cosmetics and toiletries in aqueous or hydroalcoholic solution, oil-in-water or water-in-oil emulsion, aqueous or anhydrous gels, cream, ointment, lotion, gel, solution and suspension; therapeutics and over-the-counter pharmaceutical products, water-based paints, cutting oils, latex solutions, food products such as beverages, frozen foods, candy and canned products.

In some embodiments, the formulation of the invention is an antimicrobial preservative, attesting to the ability of the formulations of the invention to suppress microbial growth, reduce microbial infestation, treat products or surfaces to improve product resistance to microbial infestation, reduce biofilm, prevent conversion of bacteria to biofilm, prevent or inhibit microbial infection, prevent spoilage, retard or minimize or prevent quorum sensing, and retard microbial reproduction. Typically, the preservative formulation according to the invention comprises the saponin and plant extract(s) at a concentration which suffices to prevent spoilage or growth of microorganisms, thereby extending the shelf- or useful-life of the product.

The pathogens against which the preservative formulation may be effective include a wide spectrum of microorganisms such as bacteria, fungi, yeast, mold, archaea, protists, viruses and algae, as listed and disclosed hereinabove.

The formulation of the invention may also be employed as a disinfectant or bacteriocide agent. The formulations of the invention may be applied onto a surface to be disinfected, including human or animal skin, by various means including by washing, spraying, wiping, etc.

MODES FOR CARRYING OUT THE INVENTION

The following description is provided, alongside all chapters of the present invention, so as to enable a person skilled in the art to make use of said invention. The examples provided herein are representative of techniques employed by the inventors in carrying out aspects of the present invention. It should be appreciated that while these techniques are exemplary of certain embodiments for the practice of the invention, those of skill in the art, in light of the present disclosure, will recognize that numerous modifications can be made without departing from the spirit and intended scope of the invention.

The present invention is directed to a formulation comprising a saponin material and a plant extract as disclosed hereinabove.

General Preparation of the Extracts

As used herein, the term "extract" refers to an active ingredient or fraction isolated from a plant by using a solvent or a solvent system. The solvent can be chosen from water or from commonly used organic solvents such as alcohols, especially lower alcohols such as methanol, ethanol, propanol, iso-propanol and butanol; alkanes such as pentane and hexane, petroleum ether 40-60 or 60-80; chlorinated alkanes such as dichloromethane and dichloroethane; aromatic solvents such as toluene and xylene; ethers such as diethyl ether; ethyl acetate and any other solvent commonly known to the person versed in the art.

The extraction procedure for obtaining any of the plant extracts employed in accordance with the invention, unless otherwise indicated, may be carried out in any commonly used technique and variation known in the art as described for example in M. Casey, J. Leonard, B. Lygo, and G. Procter *"Advanced Practical organic Chemistry"*, 1990, Chapman & Hall, London. For example, the plant parts can be crushed and/milled and optionally dried before being contacted with the extraction solvent; the extraction can be assisted with shaking or agitating, heating; the extraction can be microwave and/or ultrasound assisted; brine may be used instead of water; the solvent can be filtered and reduced under reduced pressure evaporation; the filtered solids may be re-extracted to yield a second crop; and so forth.

Extracts of at least one plant species of a genus selected from *Lonicera, Populus, Salix* and *Wasabia* are commercially available and may be used without further purification. For example *Populus tremuloides* extract can be purchased from Active Micro Systems (USA); *Lonicera japonica* can be purchased from Campo (Singapore), *Salix* American Botanicals (USA) and *Wasabi japonica* from Active concepts (Italy).

The saponin material may be similarly attained, or may be extracted from a plant source, as disclosed hereinabove, by solvent extraction employing aqueous alcohol. The water/alcohol solvent system that is used according to some embodiments is in the ratio of between 90:10 to 10:90. In some embodiments, the water/alcohol ratio is between 70:30 to 30:70. In other embodiments, the water/alcohol ratio is between 60:40 to 40:60. In other embodiments, the water/alcohol ratio is between 50:50 to 40:60.

The alcohol used in the extraction is selected from methanol, ethanol, propanol, iso-propanol and butanol. According to some embodiments, the solvent system used for extraction of saponins is water/ethanol 50:50.

According to some embodiments of the invention, the saponin is extracted from *Sapindus Mukorossi* or *Camellia oleifera* by 50:50 water/ethanol extraction solution. The extraction is performed on pericarp of *Sapindus Mukorossi* or the defatted seed meal of *Camellia oleifera*. The extraction is continued over a period of 2-8 hours at a temperature above room temperature; the extraction may be carried out at a neutral to acidic pH.

As may be understood, the saponin containing extract may also contain a variety of natural products such as acyclic sesquiterpene oligoglycosides (ASOGs).

EXAMPLES

Example 1

Extractions of *Sapindus Mukorossi* and *Camellia oleifera* by Using Various Ethanol/Water Mixtures

*Sapindus Mukorossi* extract-100 grams of dried pericarp of *Sapindus Mukorossi* were added to 400 ml water/ethanol 30:70 or 50:50 or 70:30 (w/w) in a shaker (Innova 4000 incubator shaker, New Brunswick scientific Edison, N.J. USA, rpm 183), for two hours. The shaker was heated to 60° C. The solution was filtered through Whatman 1 (Qualitative 110 mm Ø×100 circles). Then, the water mixture was expelled by Spray Dryer (SD-05, LabPlant, UK, pump rate: 0.01, inlet temperature 120° C., powdered Temp 70° C.), and a white-brown powdered was obtained (12.5-17% yield).

*Camellia oleifera* extract-100 grams of seed cake of *Camellia oleifera* were dipped in 400 ml water/ethanol 50:50 (wt %/wt %) in a shaker (Innova 4000 incubator shaker, New Brunswick scientific, Edison, N.J. USA, rpm 183), for two, four or six hours. The shaker was heated to 60° C. The solution was filtered through Whatman 1, Qualitative 110 mm Ø×100 circles). Then, the water mixture was expelled by Spray Dryer (SD-05, LabPlant, UK, pump rate: 0.01, inlet temperature 120° C., powdered Temp 70° C.), and white-brown powdered was obtained. The yield was measured at between 17 and 22%.

Example 2

Extraction of *Sapindus Mukorossi* by 50:50 Water/Ethanol Mixtures 100 grams of dried pericarp of *Sapindus Mukorossi* were added to 400 ml water/ethanol 50:50 (w/w) in a shaker (Innova 4000 incubator shaker, New Brunswick scientific Edison, N.J. USA, rpm 183), for two, four or six hours. The shaker was heated to 40° C. The solution was filtered through Whatman 1 (Qualitative 110 mm Ø×100 circles). Then, the water mixture was expelled by Spray Dryer (SD-05, LabPlant, UK, pump rate: 0.01, inlet temperature 120° C., powder Temp 70° C.), and a white-brown powder was obtained.

Example 3

Preparation of a Composition Comprising Saponins 20 g of solid Sapindus Mukorossi (extract prepared by using the water/ethanol solvent system (50:50) according to Example 2) was dissolved in a phosphate buffer. A mixture of a 1:1:1 Wasabia japonica extract/Populus tremuloides extract/Lonicera japonica mixture (herein "WPL") was dissolved in a phosphate buffer. The mixtures were stirred and then diluted in a phosphate buffer to obtain seven compositions: 0:0, 0.2:2, 0.2:10, 0.2:20, 0.1:20, 0.05:20, 0.01:20, 0:20 wt % (1:1:1 WPL/Sapindus Mukorossi extract) solutions. The solutions were heated overnight to 50° C. to obtain sterile solutions.

Example 4

Demonstrated Effect in a Challenge Test

The tests were conducted by adding to: (a) sterile solutions of the compositions prepared in Example 3, (b) a 20 wt % sterile solution of Sapindus Mukorossi extract and (c) a sterile solution of the 1:1:1 WPL mixture of Example 3 an inoculum of suitable microorganisms (bacteria and yeast), as described below. The so-prepared solutions were stored at 37° C. for bacteria or 30° C. for yeast. Using serial dilutions and plate counts, aliquots were taken during the incubation period for determining microorganism count.

Media and Reagents Used:

phosphate buffer 100 mM pH=5.5 (sterile), TSYE (30 g/l/l tryptic soy broth+5 gr/l yeast extract) was added to a solid media 2% agar, PDB (24 g/l potato dextrose broth+0.2 g/l chloramphenicol) was added to a solid media 2% agar and a diluent (a sterile solution of 0.9% sodium chloride and 0.1% peptone) was used when indicated.

The tested organisms were Salmonella typhimurium ATCC 14028, Escherichia coli EDL933, Staphylococcus aureus MRSA strain Newman D2 ATCC 25904 and Saccharomyces cerevisiae ATCC 11777. The three bacteria were grown overnight on TSYE, in an incubator shaker at 37° C. Yeast cells were grown overnight on PDB, in an incubator shaker at 30° C. The media from the overnight cultures were washed twice with the diluent by centrifugation and each one of the organisms was transferred to 5 ml of the phosphate buffer containing different extract combinations to yield $10^5$/ml. The test tubes were incubated either at 37° C. for the bacteria or 30° C. for the yeast. Aliquots were taken during the incubation period for the purpose of determining microorganism count. The numbers in the table are the means of two separate experiments. Each treatment was repeated three times.

TABLE 1 total count of different microorganisms as a function of the cocktail preservatives and Sapindus mukorossi extract concentrations

| Microorganisms | WPL extracts mixture/Sapindus extract wt % | | | | |
|---|---|---|---|---|---|
| | 0/0 | 0.2/0 | 0.2/2 | 0.2/10 | 0.2/20 |
| E. Coli | $10^5$ | $5 \times 10^2$ | <10 | <10 | <10 |
| Salmonella | $10^5$ | $5 \times 10^4$ | $2 \times 10^3$ | <10 | <10 |
| Staphylococcus | $10^5$ | $10^4$ | $10^4$ | $10^4$ | <200 |
| Saccharomyces | $10^5$ | $10^5$ | $10^3$ | 200 | 200 |
| | 0/0 | 0/20 | 0.01/20 | 0.05/20 | 0.1/20 |
| E. Coli | $10^5$ | $10^5$ | $10^5$ | <10 | <10 |
| Salmonella | $10^5$ | $10^6$ | $10^6$ | $10^3$ | <10 |
| Staphylococcus | $10^5$ | <200 | <200 | <200 | <200 |
| Saccharomyces | $10^5$ | $10^3$ | $10^3$ | 200 | 200 |

As can be seen from the Table 1, except for the case of Staphylococcus, the WPL extract mixture by itself or the Sapindus extract by itself did not reduce the total microorganism count below 1000. As for Staphylococcus, the WPL extract itself reduced the count by a factor of 10 while the Sapindus extract reduced it by 3 orders of magnitude. Thus, overall, the combination of the WPL extract mixture and the Sapindus extract reduced the total microorganisms count below 10. These surprising results indicate a synergistic effect between the Sapindus extract and the preservatives cocktail.

Example 5

Antimicrobial Effectiveness Testing (USP 32, 2009)

The test was performed according the requirements of the US Pharmacopoeia 32 2009, (51) Antimicrobial Effectiveness Testing.

The test was conducted on 100 g samples of a shampoo formulation comprising 81.1% water, 10% soap nut extract, 4% Betaine, 2% Phospholipon 50 (Lipoid), 2% Guar-gum, 0.3% Xanthan-gum, 0.3% Aspen extract (Active Micro Systems), 0.3% Fragrance mixture (Expressions Parfumees). This formulation is herein referred to as formulation MC-6.

Each sample was separately inoculated by one of the five test organisms. The inoculated containers were incubated in 25° C. together with an uninoculated sample. The number of surviving microorganisms was monitored periodically during an incubation of 4 weeks and the colony forming units (CFU)—were counted by a plate counter.

The tested microorganisms were:

1. E. coli ATCC 8739
2. Staphylococcus aureus ATCC 6538
3. Pseudomonas aeruginosa ATCC 9027
4. Candida albicans ATCC 10231
5. Aspergillus niger ATCC 16404

TABLE 2 total count for different microorganisms after contact with the MC-6 formulation

| Organism | | Initial Contamination [CFU/gr] | No. of Surviving Microorganisms CFU/gr | | | |
|---|---|---|---|---|---|---|
| | | | 1 week | 2 weeks | 3 weeks | 4 weeks |
| E. coli | 8739 | $8.2 \times 10^5$ | $4.3 \times 10^2$ | <10 | <10 | <10 |
| S. aureus | 6538 | $8.9 \times 10^5$ | $5.5 \times 10^3$ | <10 | <10 | <10 |
| P. aeruginosa | 9027 | $8.3 \times 10^5$ | $5.2 \times 10^3$ | <10 | <10 | <10 |
| C. albicans | 10231 | $2.5 \times 10^5$ | $4 \times 10^2$ | <10 | <10 | <10 |
| A. niger | 16404 | $3.1 \times 10^5$ | $2.8 \times 10^4$ | <10 | <10 | <10 |
| Uninoculated Control | | <10 | <10 | <10 | <10 | <10 |

As can be seen from Table 2, formulation MC-6 reduced total counts for all microorganisms tested to below 10 after 2 weeks of incubation and prevented re-growth for at least an additional two weeks. The uncontaminated sample remained uncontaminated.

Example 6

Antimicrobial Effectiveness Testing (USP 32, 2009)—Re-Challenge

The test was performed according the requirements of the US Pharmacopoeia 32 2009, (51) Antimicrobial Effectiveness Testing.

The test was conducted on 100 g samples that were previously used in the challenge test and showed a total count of below 10 CFU/gr after four weeks. Each sample was separately re-inoculated by one of the same five test microorganisms.

The inoculated containers were incubated in 25° C. together with an uninoculated sample. The number of surviving microorganisms was checked after an incubation of 4 weeks.

TABLE 3 total count for different microorganisms re-inoculated in the MC-6 formulation

| The Organism | | Initial Contamination CFU/gr | No. of Surviving Microorganisms CFU/gr 4 week |
|---|---|---|---|
| E. coli | 8739 | $3.2 \times 10^5$ | <10 |
| S. aureus | 6538 | $5.9 \times 10^5$ | <10 |
| P. aeruginosa | 9027 | $3.3 \times 10^5$ | <10 |
| C. albicans | 10231 | $6.5 \times 10^5$ | <10 |
| A. niger | 16404 | $4.5 \times 10^5$ | <10 |
| Uninoculated Control | | <10 | <10 |

As can be seen from Table 3, formulation MC-6 reduced the total counts for all re-inoculated microorganisms tested to below 10 after 4 weeks of incubation. The uncontaminated sample remained uncontaminated.

Example 7

Identifying the Active Fraction in the Soap-Nut Extract in Synthetic Soap

Media and reagents used: citric acid-$Na_2HPO_4$ buffer (150 mM pH=5.6) and TSYE (30 gr/l tryptic soy broth+5 gr/l yeast extract) were added to a solid media 2% agar and a diluent (a sterile solution of 0.1% peptone) was used where indicated.

The tested organisms were *Salmonella typhimurium* ATCC 14028.

The bacteria were grown overnight on TSYE in an incubator shaker at 37° C. The media from the overnight cultures were washed twice with the diluent by centrifugation and the organisms transferred to 5 ml of the citric acid-$Na_2HPO_4$ buffer containing different combinations of soap, Aspen (*Populus tremuloides*) bark extract and saponin to yield $10^5$ CFU/ml.

10% Soap (Ammonium lauryl sulfate (6.6%)+cocamidopropyl betaine (3.3%)) was added with 0.1% Aspen bark extract and one of (1) 2% soap-nut extract, or (2) 2% saponin fraction (Ethyl-acetate soluble) of the soap-nut extract, or (3) 2% ASOGS fraction (water soluble) of the soap-nut extract. The test tubes were incubated at 30° C. Aliquots were taken during the incubation period for determining microorganism count. The numbers presented in Table 4 are the mean of two separate experiments. Each treatment was repeated three times.

TABLE 4 total count for *Salmonella* in soap containing different fractions of the soap-nut extract

| No. | Soap (10%) | soap-nut extract (2%) | saponin (2%) | ASGOS (2%) | Preservative Aspen (0.1%) | *Salmonella* (CFU/ml) t = 24 h | *Salmonella* (CFU/ml) t = 72 h |
|---|---|---|---|---|---|---|---|
| 1 | + | + | − | − | − | $10^8$ | $10^8$ |
| 2 | + | − | + | − | − | $3.4 \times 10^5$ | $8 \times 10^5$ |
| 3 | + | − | − | + | − | $10^8$ | $10^8$ |
| 4 | + | + | − | − | + | $4 \times 10^5$ | $2 \times 10^5$ |

TABLE 4-continued total count for Salmonella in soap containing
different fractions of the soap-nut extract

| No. | Soap (10%) | soap-nut extract (2%) | saponin (2%) | ASGOS (2%) | Preservative Aspen (0.1%) | Salmonella (CFU/ml) t = 24 h | Salmonella (CFU/ml) t = 72 h |
|---|---|---|---|---|---|---|---|
| 5 | + | − | + | − | + | $2.4 \times 10^5$ | $2.2 \times 10^2$ |
| 6 | + | − | − | + | + | $10^7$ | $10^8$ |

As can be seen from Table 4, the combination of 10% Soap with 0.2% Aspen bark extract (*Populus tremuloides*) and 2% of the saponin fraction reduced *Salmonella* total counts by 6 logs after just 72 h of incubation.

Example 8

Reducing the Concentration of Aspen Bark (*Populus tremuloides*) Extract

Media and reagents used: phosphate buffer 100 mM pH=5.5 and TSYE (30 gr/l tryptic soy broth+5 gr/l yeast extract) were added to a solid media 2% agar, PDB (24 gr/l potato dextrose broth+0.2 gr/l chloramphenicol) was added to a solid media 2% agar and a diluent (a sterile solution of 0.1% peptone) was used where indicated.

The tested organism was *Salmonella typhimurium* ATCC 14028. The bacteria were grown overnight on TSYE in an incubator shaker at 37° C. The media from the overnight cultures was washed twice with the diluent by centrifugation and the organisms were transferred to 5 ml of the phosphate buffer containing different combinations of Soap-nut extract (10% wt solids) and different concentrations of Aspen bark extract (*Populus tremuloides*) to yield 105 CFU/ml. The test tubes were incubated at 37° C. for 14 days. Aliquots were taken during the incubation period for determining microorganism count. The numbers presented in Table 5 are the mean of two separate experiments. Each treatment was repeated three times.

TABLE 5 total counts for *Salmonella typhimurium*
as a function of concentration

| Soap-nut extract (% wt solids) | Aspen bark extract (*Populus tremuloides*) (wt/v %) | CFU/ml |
|---|---|---|
| 10 | 0.4 | <10 |
| 10 | 0.1 | 115 |
| 10 | 0.05 | $2 \times 10^4$ |
| — | — | $2.5 \times 10^6$ |

As can be seen from Table 5, the preservative effect of Aspen bark extract (*Populus tremuloides*) was quantitative and even as little as 0.1% caused a 4 log reduction in the total counts of *Salmonella*.

Example 9

Testing Different Saponins with Synthetic Soap

Media and reagents used: citric acid-Na$_2$HPO$_4$ buffer 150 mM pH=5.6 and TSYE (30 gr/l tryptic soy broth+5 gr/l yeast extract) were added to a solid media 2% agar and a diluent (a sterile solution of 0.1% peptone) was used where indicated.

The tested organism was *Salmonella typhimurium* ATCC 14028. The bacteria were grown overnight on TSYE in an incubator shaker at 37° C. The media from the overnight cultures was washed twice with the diluent by centrifugation and the organisms transferred to 5 ml of the citric acid-Na$_2$HPO$_4$ buffer containing different combinations of soap, Aspen bark extract and saponin or only Aspen bark to yield $10^5$ CFU/ml. 10% Soap (Ammonium lauryl sulfate (20%)+ cocamidopropyl betaine (10%)) was added with 0.2% of Aspen bark extract (*Populus tremuloides*) and one of (1) 1% tea saponin, (2) 2% of soap-nut extract. The test tubes were incubated at 30° C. Aliquots were taken during the incubation period for determining microorganism count. The numbers presented in Table 6 are the mean of two separate experiments. Each treatment was repeated three times.

TABLE 6 total counts for *Salmonella* in soap containing different saponins

| Tube no. | Soap (10%) | Saponin type | Aspen bark extract (*Populus tremuloides*) (0.2%) | *Salmonella typhimurium* (CFU/ml) t = 72 h | *Salmonella typhimurium* (CFU/ml) t = 10 days |
|---|---|---|---|---|---|
| 1 | − | — | − | $3.7 \times 10^7$ | $3 \times 10^7$ |
| 2 | − | — | + | $1.7 \times 10^6$ | $3 \times 10^4$ |
| 3 | + | — | + | $1.1 \times 10^3$ | <10 |
| 4 | + | Tea saponin (1%) | + | <10 | <10 |
| 5 | + | Soap-nut extract (2%) | + | <10 | <10 |

As can be seen from Table 6, the combination of 10% Soap with 0.2% Aspen bark extract (*Populus tremuloides*) and either 1% tea saponin or 2% soap-nut extract reduced *Salmonella* total counts to below 10 even after just 72 h of incubation.

Example 10

Reducing the Amount of Aspen Bark (*Populus tremuloides*) Extract in Synthetic Soap Media and reagents used: citric acid-Na$_2$HPO$_4$ buffer 150 mM pH=5.6 and TSYE (30 gr/l tryptic soy broth+5 gr/l yeast extract) were added to solid media 2% agar, PDB (24 gr/l potato dextrose broth+0.2 gr/l chloramphenicol) was added to a solid media 2% agar and a diluent (a sterile solution of 0.1% peptone) was used where indicated.

The tested organisms were *Salmonella typhimurium* ATCC 14028 and *Aspergillus niger* ATCC 16404. The bacteria were grown overnight on TSYE in an incubator shaker at 37° C. The fungi were grown on PDB+agar for three weeks in an incubator at 30° C. and conidia harvested in 0.15% Tween 80. The media from the cultures were washed twice with the diluent by centrifugation and the organisms transferred to 5 ml of the citric acid-Na$_2$HPO$_4$ buffer containing different combinations of soap, preservative and saponin to yield 10$^5$CFU/ml. Soap (Ammonium lauryl sulfate (20%)+cocamidopropyl betaine (10%)) was added at 10% with 2% of soap-nut extract and varying amounts of Aspen bark extract (Populus tremuloides). The test tubes were incubated at either 30° C. for bacteria or 24° C. for fungi. Aliquots were taken during the incubation period for determining microorganism count. The numbers presented in Table 7 are the mean of two separate experiments. Each treatment was repeated three times.

TABLE 7 total counts for Salmonella and Aspargillus in soap containing varying concentrations of Aspen bark extract (Populus tremuloides).

| Treat | Soap 10% | Soap-nut extract 2% | Aspen bark extract Populus tremuloides (%) | Salmon. T = 24 h | Salm. 96 h | Salm. 7 days | Salm. 14 days | A. nig 96 h | A. nig 7 days | A. nig 14 days |
|---|---|---|---|---|---|---|---|---|---|---|
| 1 | − | − | — | 3.7 × 10$^6$ | 1 × 10$^6$ | 1 × 10$^6$ | 7 × 10$^5$ | 2 × 10$^3$ | 4 × 10$^3$ | 1.3 × 10$^4$ |
| 8 | + | − | — | 3.9 × 10$^5$ | 1 × 10$^6$ | N/A | >10$^8$ | >10$^3$ | >10$^3$ | 4 × 10$^3$ |
| 11 | + | − | 0.1 | 4.5 × 10$^5$ | <10 | 4 × 10$^7$ | 3 × 10$^7$ | >10$^3$ | >10$^3$ | 2.3 × 10$^3$ |
| 12 | + | − | 0.05 | 4.7 × 10$^5$ | 1 × 10$^6$ | 8 × 10$^7$ | 3 × 10$^7$ | >10$^3$ | 3 × 10$^2$ | 7.2 × 10$^3$ |
| 13 | + | + | — | 4.9 × 10$^5$ | 1 × 10$^5$ | 2 × 10$^5$ | 2 × 10$^5$ | >10$^3$ | <10 | <10 |
| 34 | + | + | 0.1 | 2.9 × 10$^5$ | 6 × 10$^2$ | <10 | <10 | >10$^3$ | <10 | <10 |
| 37 | + | + | 0.05 | 2.9 × 10$^5$ | 2.6 × 10$^4$ | 10$^4$ | 4 × 10$^5$ | >10$^3$ | <10 | <10 |

As can be seen from Table 7, the amount of Aspen bark extract (Populus tremuloides) could be reduced to as little as 0.1%. Even at this reduced amount the total counts of Salmonella was reduced to below 10. The combination of soap and 2% soap-nut saponin alone was sufficient to reduce total counts of Aspergillus to below 10.

Example 11

Determining the Active Component in the Preservative Formulation

Media and reagents used: phosphate buffer 100 mM pH=5.5 and TSYE (30 gr/l tryptic soy broth+5 gr/l yeast extract) were added to a solid media 2% agar and PDB (24 gr/l potato dextrose broth+0.2 gr/l chloramphenicol) was added to a solid media 2% agar and a diluent (a sterile solution of 0.1% peptone) was used where indicated.

The tested organisms were Salmonella typhimurium ATCC 14028 and Saccharomyces cerevisiae ATCC 11777. The bacteria were grown overnight on TSYE in an incubator shaker at 37° C. Yeast cells were grow overnight on PDB in an incubator shaker at 30° C. The media from the overnight cultures were washed twice with the diluent by centrifugation and each of the organisms was transferred to 5 ml of the phosphate buffer containing different combinations of Soap-nut extract (10% wt solids) and either Aspen bark extract (Populus tremuloides), Wasabi extract (Wasabia japonica) or Japanese Honeysuckle extract (Lonicera Japonica) at 0.7% wt to yield 10$^5$ CFU/ml. The test tubes were incubated at either 37° C. for bacteria or 30° C. for the yeast. Aliquots were taken during the incubation period for determining microorganism count. The numbers presented in Table 8 are the mean of two separate experiments. Each treatment was repeated three times.

TABLE 8 total counts for Salmonella as a function of the Soap-nut extract (10% wt solids) and preservative combination.

| Plant extract (0.7%) | Soap-nut extract (10% wt solids) (10%) | Salmonella |
|---|---|---|
| Aspen bark extract (Populus tremuloides) | − | 1 × 10$^5$ |
| Wasabi extract (Wasabia japonica) | − | 4.5 × 10$^5$ |

TABLE 8-continued total counts for Salmonella as a function of the Soap-nut extract (10% wt solids) and preservative combination.

| Plant extract (0.7%) | Soap-nut extract (10% wt solids) (10%) | Salmonella |
|---|---|---|
| Japanese Honeysuckle extract (Lonicera Japonica) | − | 4 × 10$^5$ |
| Aspen bark extract (Populus tremuloides) | + | <10 |
| Wasabi extract (Wasabia japonica) | + | 6 × 10$^5$ |
| Japanese Honeysuckle extract (Lonicera Japonica) | + | >10$^7$ |
| — | + | >10$^7$ |
| — | − | 6.5 × 10$^5$ |

As can be seen from Table 8, the soap-nut extract (10% wt solids) alone or the different plant extracts alone, did not reduce the salmonella count. Only the combination of soap-nut extract (10% wt solids) with a natural plant extract such as Aspen bark extract (Populus tremuloides) caused the total microorganism count to drop below 10. These surprising results indicate a synergistic effect between the Soap-nut extract (10% wt solids) and Aspen bark extract (Populus tremuloides).

Example 12

Determining In Vivo Effectiveness

The effectiveness of formulations of the invention as antimicrobial agents in-vivo can be tested in vitro or in vivo by a variety of methods known in the art for testing antimicrobial activity. See, for example, the methods discussed herein and used throughout the examples.

A number of assays may be employed in accordance with the present invention in order to determine the degree of antimicrobial activity of a compound of the invention such as cell culture, animal models, and administration to human subjects. The assays described herein may be used to assay microbial growth over time to determine the growth characteristics of a microbe in the presence of a formulation of the invention.

A microbe and a formulation of the invention are added to a permissive cell line (e.g. primary cells, transformed cell lines, patient tissue samples, etc) or growth medium (e.g. LB broth/agar, YT broth agar, blood agar, etc.). The growth/infection of the microbe can be compared to the growth/infection of the microbe in the absence of the formulation of the invention. Antimicrobial activity of the formulation of the invention is demonstrated by a decrease in microbe growth/infection in the presence of the formulation of the invention. Any method known in the art can be used to determine the growth infection, including, but not limited to, immunofluorescent staining, immunoblot or detection of a microbe-specific nucleic acid (e.g., by in situ hybridization, or after cell lysis by Southern blot or RT-PCR analysis), visual/microscopic inspection for cytopathic effect of growth infection (e.g., for microbes that are viruses cell rounding, cell detachment, cell lysis, formation of multinucleated syncytia), microbe titer (e.g., plaque forming units, colony forming units, etc.), number of plaques colonies.

The microbe and the formulation of the invention may be added to the cells or growth medium at the same time or alternatively the microbe may be added to the cells or growth medium before the formulation of the invention is added. As may be required, the formulation of the invention may be added to the cells or growth medium before the microbe is introduced to the cells or growth medium.

A microbe and a formulation of the invention may be administered to animal subjects susceptible to infection with the microbe. The incidence, severity, length, microbe load, mortality rate of infection, etc. can be compared to the incidence, severity, length, microbe load, mortality rate of infection, etc. observed when subjects are administered the microbe alone (in the absence of a formulation of the invention). Antimicrobial activity of the formulation of the invention is demonstrated by a decrease in incidence, severity, length, microbe load, mortality rate of infection, etc. in the presence of the formulation of the invention.

The microbe and the formulation of the invention may be administered to the animal subject at the same time, or one after the other.

The growth rate of the microbe can be tested by sampling cell culture medium or biological fluids/clinical samples (e.g., nasal aspirate, throat swab, sputum, broncho-alveolar lavage, urine, saliva, blood, or serum) from human or animal subjects at multiple time points post-infection either in the presence or absence of a formulation of the invention and measuring levels of microbe. In specific cases, the growth rate of a microbe may be assayed by assessing the presence of microbe in a sample after growth in cell culture, growth on a permissible growth medium, or growth in subject using any method well-known in the art, for example, but not limited to, immunoassay (e.g., ELISA; for discussion regarding ELISAs see, e.g., Ausubel et al, eds., 1994, Current Protocols in Molecular Biology, Vol. 1, John Wiley and Sons, New York at 11.2.1), immunofluorescent staining, or immunoblot analysis using an antibody which immunospecifically recognizes the microbe to be assayed or detection of a microbe-specific nucleic acid (e.g., by Southern blot or RT-PCR analysis, etc.).

The invention claimed is:

1. A composition comprising an anti-bacterially effective amount of a saponin material from at least one plant selected from the group consisting of *Camellia sinensis, Camellia oleifera, Saponaria officinalis*, and *Sapindus mukorossi* or a mixture thereof, and an anti-bacterially effective amount of a plant extract from at least one plant selected from the group consisting of *Lonicera, Populus*, and *Wasabia* or a mixture thereof,
    wherein the weight ratio between the saponin material and the plant extract is between about 1:100 and about 100:1.

2. The composition according to claim 1, wherein the saponin material is selected from the group consisting of a saponin-containing extract or a saponin compound obtained from the at least one plant selected from the group consisting of *Camellia sinensis, Camellia* oleifera, *Saponaria officinalis*, and *Sapindus mukorossi* or a mixture thereof.

3. The composition according to claim 2, wherein the saponin-containing extract is obtained by extraction of said plant with water, alcohol, or a water/alcohol mixture.

4. The composition according to claim 3, wherein the water/alcohol mixture has a water:alcohol ratio selected from a ratio of between 80:20 and 20:80, a ratio of between 60:40 and 40:60, a ratio of between 70:30 and 30:70, and a ratio of 50:50, respectively.

5. The composition according to claim 2, wherein the saponin-containing extract is extracted from said plant by a method comprising:
    a) extracting the plant in a water:alcohol solution having a water:alcohol ratio of between 40:60 and 60:40 for a suitable period of time;
    b) optionally, evaporating the extract to a obtain a solid saponin-containing extract; and
    c) optionally, purifying one or more saponin compounds from said solid saponin-containing extract.

6. The composition according to claim 5, wherein the water:alcohol ratio is 50:50.

7. The composition according to claim 6, wherein the plant is *Camellia oleifera* or *Sapindus mukorossi*.

8. The composition according to claim 1, wherein the *Lonicera* extract is an extract of *Lonicera japonica*.

9. The composition according to claim 1, wherein the *Populus* extract is an extract of aspen.

10. The composition according to claim 9, wherein the extract is of *Populus tremuloides*.

11. The composition according to claim 1, wherein the *Wasabia* extract is an extract of *Wasabia japonica*.

12. The composition according to claim 1, wherein the weight ratio between the saponin material and the plant extract is between about 1:1 and about 10:1, respectively.

13. The composition according to claim 1, wherein the plant extract comprises a 1:1:1 ratio of *Wasabia japonica* extract, *Populus tremuloides* extract, and *Lonicera japonica* extract.

14. A product comprising an anti-bacterially effective amount of the composition of claim 1, wherein the product is selected from the group consisting of a preservative formulation, an antimicrobial formulation, a pharmaceutical composition, a disinfectant, and a cosmetic product.

* * * * *